United States Patent [19]

Rösch et al.

[11] Patent Number: 4,721,801
[45] Date of Patent: Jan. 26, 1988

[54] PROCESS FOR THE PREPARATION OF ORGANOHALOSILANES

[75] Inventors: Lutz Rösch, Kempten; Günter Kratel, Durach-Bechen; Anton Stroh, Munich, all of Fed. Rep. of Germany

[73] Assignee: Wacker-Chemie GmbH, Munich, Fed. Rep. of Germany

[21] Appl. No.: 28,337

[22] Filed: Mar. 20, 1987

[30] Foreign Application Priority Data

Mar. 26, 1986 [DE] Fed. Rep. of Germany ....... 3610267

[51] Int. Cl.$^4$ .............................. C07F 7/08; C07F 7/12
[52] U.S. Cl. ..................................... 550/478
[58] Field of Search ........................................ 556/478

[56] References Cited

U.S. PATENT DOCUMENTS 2,949,481  8/1960  Anderson et al. ................... 556/478
3,004,079 10/1961  Sleddon et al. ................. 556/478 X

FOREIGN PATENT DOCUMENTS 0805674 12/1958  United Kingdom ........ 556/478 UX
0218888  8/1969  U.S.S.R. ............................... 556/478

Primary Examiner—Paul F. Shaver
Attorney, Agent, or Firm—Collard, Roe & Galgano

[57] ABSTRACT

A process for the preparation of an organohalosilane of the general formula:

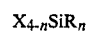

$$X_{4-n}SiR_n$$

in which,

R represents a methyl, ethyl, n-propylisopropyl, n-butyl, isobutyl, phenyl or a tolyl functional group;
X represents chlorine or bromine; and
n is 1, 2 or 3, is disclosed. The process takes place by reacting an $SiO_2$-containing material with a hydrocarbon halide of the general formula RX, in which R and X are defined as above. The reaction between the $SiO_2$-containing material and RX takes place in the presence of iron powder and either: (a) carbon and a catalyst, in which the $SiO_2$-containing material, the iron powder, the carbon and the catalyst are subjected to a heat treatment at 800° to 1400° C. prior to the reaction with RX or (b) an aluminum trihalide and/or boron trihalide in which the halogen is either chlorine or bromine. Alternative (b) may be carried out in the presence of a catalyst. The organohalosilanes of the invention are useful, for example, as starting materials for the preparation of organopolysiloxanes and as starting materials for the preparation of SiC produced in the gas phase.

19 Claims, No Drawings

PROCESS FOR THE PREPARATION OF ORGANOHALOSILANES

The present invention relates to a process for the preparation of organohalosilanes. Organohalosilanes are employed in large quantities as starting materials for the preparation of, for example, organopolysiloxanes. Organohalosilanes are also used, for example, as starting materials for the preparation of SiC produced in the gas phase.

Presently known methods for synthesizing organohalosilanes on a large manufacturing scale proceed via the reduction of $SiO_2$-containing material to give elementary silicon or ferrosilicon. Products based on silicon, including organohalosilanes and secondary products prepared therefrom on a large manufacturing scale, are therefore burdened with a high-energy synthesis stage.

It is already known, in accordance with British Patent specification No. 805,674 how to obtain organohalosilanes and organosilanes from $SiO_2$-containing material by reacting the latter with alkylaluminum halides or, optionally, with aluminum and a hydrocarbon halide in the presence of a catalyst. This process thus makes it possible, in principle, to prepare organohalosilanes from $SiO_2$-containing material. It is, however, a disadvantage in the British process that this process must be carried out to the exclusion of moisture and oxygen, since the alkylaluminum halides, which are also formed in situ in the reaction with aluminum and a hydrocarbon halide, react explosively with water or are self-igniting. Accordingly, extensive protective measures are required which limit the applicability of this process on a large manufacturing scale. Furthermore, aluminum is used in this process and its isolation requires a great expenditure of energy.

It is, therefore, an object of the present invention to provide a process for the synthesis of organohalosilanes and for the preparation of secondary products of organohalosilanes which is more efficient, requires less energy and is, therefore, more economical than known methods which proceed via a reaction stage leading to elementary silicon.

The foregoing and related objects are attained by a process for the preparation of organohalosilanes of the general formula $$X_{4-n}SiR_n$$

wherein
R is methyl, ethyl, n-propyl, isopropyl, n-butyl, isobutyl, phenyl or tolyl;
X is Cl or Br; and
n is 1, 2 or 3,
by reaction of $SiO_2$-containing material with a hydrocarbon halide of the formula $$RX$$

wherein R and X are defined as above, in the presence of a metal or metal halide and, optionally, with the addition of a catalyst, characterized in that the reaction is carried out in the presence of iron powder and (a) carbon and a catalyst, in which case the $SiO_2$-containing material, the iron powder, the carbon and the catalyst are subjected to a heat treatment at 800° to 1400° C. before the reaction with RX; or (b) an aluminum trihalide and/or boron trihalide, wherein the halogen is chlorine or bromine and, optionally, in the presence of a catalyst in which the catalyst represents elements of the 1st, 2nd or 8th subgroup of the periodic system of elements and, further, halides or oxides of such elements.

The elements of the 1st, 2nd or 8th subgroup of the periodic system of the elements can be seen from the Periodic Table of the Elements according to Mendeleev in the Handbook of Chemistry and Physics, 61st edition, on the inner page of the cover, under Transition Elements Groups 1b, 2b and 8.

$SiO_2$-containing material employed in accordance with the invention, preferably, has an $SiO_2$ content of 40 to 100% by weight and, in particular, 70 to 100% by weight. The specific surface area, measured by the BET method, is preferably at least 0.1 m²/g and, in particular, at least 3 m²/g.

Examples of $SiO_2$-containing material which can be employed in accordance with the invention are diatomaceous earth, silica, e.g., assiliceous chalk, montmorrillonite, magnesium silicate, clays, e.g., bentonite and kaolin, zeolites of low aluminum content, $SiO_2$-containing flue dusts and the like.

Iron powder which may be employed in accordance with the invention preferably has an Fe content of 70 to 100% by weight and, in particular, 95 to 100% by weight. The specific surface area, measured by the BET method, is preferably at least 0.1 m²/g.

Carbon is preferably employed in a finely divided form. The specific surface area is preferably at least 0.5 m²/g and, in particular, at least 5 m²/g, as measured by BET.

Examples of carbon employed in accordance with the invention are carbon blacks, coke dust, active charcoal and the like.

An aluminum trihalide and/or boron trihalide, wherein the halogen is chlorine or bromine, is preferably employed either in a finely divided form or in a gaseous state. Use in the inventive process of aluminum trihalide and/or boron trihalide can be effected in any suitable form, for example, by charging the stream of hydrocarbon halide with the halide or by metering the latter in separately. It is preferable to employ aluminum trichloride for the preparation of an organochlorosilane and aluminum tribromide for the preparation of organobromosilanes.

The hydrocarbon halide can be employed in any suitable state, preferably in the gaseous state and, optionally, together with inert gas constituents, such as, for example, nitrogen or argon.

It is preferable to mix the catalysts into the starting substances in a finely divided form. Catalysts, according to the invention, are elements of the 1st, 2nd and 8th subgroup of the periodic system of the elements and halides and oxides of these elements. Preferred catalysts are Cu, Zn, Co or Ni, oxides thereof and halides thereof, particularly the chlorides and bromides. In addition to the elements mentioned, examples of the catalysts are $Cu_2O$, CuO, ZnO, CoO, $Co_3O_4$, NiO, CuCl, $CuCl_2$, CuBr, $CuBr_2$, $ZnCl_2$, $ZnBr_2$, $CoCl_2$, $CoBr_2$, $NiC_2$ and $NiBr_2$. The catalysts can be used individually or in combinations with one another.

All the elements of the 1st, 2nd and 8th subgroup of the periodic system of the elements and halides and oxides thereof constitute catalysts according to the invention. However, the possibility of using several elements, such as, for example, Ru, Os, Rh, Ir, Pd, Pt, Au and Ag is severely limited because of their great expense. The possibility of using, for example, Cd or Hg is severely limited by the considerable environmental pollution caused by such elements. The same would apply with respect to the halides and oxides of the aforesaid elements.

The $SiO_2:Fe$ molar ratio is preferably 3:1 to 1:4 and, in particular, 1:2 to 1:3; the $SiO_2:C$ molar ratio is preferably 1:2 to 1:5 and, in particular 1:3 to 1:4; and the $SiO_2:MX_3$ molar ratio (M=B or Al; X=Cl or Br) is preferably 5:1 to 1:5 and, in particular 1:1 to 1:3.

The ratio by weight of the catalyst to the amount of $SiO_2$ employed is preferably 0.01 to 0.3 part by weight and, in particular, 0.05 to 0.2 part by weight.

The process is carried out by intimately mixing $SiO_2$-containing material, Fe powder, carbon or, optionally, aluminum trihalide and, optionally, a catalyst in the ratios indicated above. Optionally, the individual components or mixtures thereof are subjected to a grinding process. The mixtures are employed in powder form, as pellets or in the form of lumps. The preparation of the pellets and shaped articles, which can, optionally, contain up to 20% by weight of a binder, can be carried out in any suitable manner, for example, by making the mixtures into a suspension or paste by means of suitable liquids, preferably, water or methylene chloride.

Examples of binders which can be used are waterglass (sodium silicate), molasses, bentonite, clays, resins, polyvinyl acetate, cellulose, starch and the like.

Examples of shaped articles in the form of which the mixtures to be reacted, in accordance with the invention, are employed are spheres, cylinders, hollow filaments, rings and the like.

The reaction is in most cases carried out in tubular reactors. Fluidized bed arrangements are preferable, particularly for continuous operation.

The reaction temperature is preferably 200° to 500° C. and, in particular, 220° to 450° C.

If carbon and a catalyst are added, the $SiO_2$-containing material, iron powder, carbon and catalyst are subjected to a heat treatment, preferably for 2 to 35 hours at 800° to 1400° C., preferably 1000° to 1300° C. and especially 1100° to 1200° C., and preferably under an inert gas, before the reaction with RX. After cooling, preferably under an inert gas, preferably, 20° to 500° C. and especially 200° to 400° C., the reaction is continued by adding the hydrocarbon halide and, optionally, by heating to the reaction temperature.

The residence time of the hydrocarbon halide totals preferably 1 to 500 seconds and, in particular, 60 to 120 seconds. It is preferable to carry out the process under the pressure of the ambient atmosphere, that is to say less than or approximately 1020 hPa. Optionally, however, it is also possible to employ higher or lower pressures.

The organohalosilanes leave the reactor in the gaseous or liquid state and are worked up in accordance with processes known to those skilled in the art by condensation and/or distillation.

The invention will now be described in greater detail by means of the following examples. It should be stressed, however, that the examples are provided for purposes of illustration, rather than as a definition of the limits or scope of the present invention.

EXAMPLE 1

75 g of $SiO_2$ dust (96.5% by weight of $SiO_2$), having a BET surface area of 20 m²/g, were thoroughly mixed with 75 g of Fe powder (99.5% by weight of Fe, 0.37 m²/g), 60 g of carbon black (26 m²/g) and 18 g of Cu powder, and the mixture was pelletized with water. The resulting granules were then dried for 2 hours at 220° C. in a vacuum cabinet. 195 g of this mixture were put into a tubular reactor and heated to 1100° C. in the course of 4 hours while argon was passed in. The reaction mixture was kept at this temperature for 13 hours. It was then allowed to cool under argon to 200° C. Methyl chloride was then passed in, instead of the argon, at 50 ml/min, and the mixture was heated again. The reaction set in at 325° C. At 350° C. all the methyl chloride was consumed. The evolution of silane lasted for 30 hours. The silane mixture obtained was 50% of the theoretical yield relative to methyl chloride employed, and was composed of 80 mole % of methyltrichlorosilane, 5 mole % of dimethyldichlorosilane and 15 mole % of tetrachlorosilane.

EXAMPLE 2

15 g of $SiO_2$ dust (96.5% by weight of $SiO_2$), having a BET surface area of 20 m²/g, were thoroughly mixed with 15 g of Fe powder (99.5% by weight of Fe, 0.37 m²/g), 6 g of carbon black (26 m²/g) and 3.6 g of Cu powder, and the mixture was mixed with quartz wool and put into a tubular reactor and heated to 1100° C. in the course of 4.5 hours, while argon was passed in. The reaction mixture was kept at this temperature for 5 hours. It was then allowed to cool under argon to 200° C. Methyl chloride was then passed in instead of the argon at 50 ml/min, and the mixture was heated again. Almost all the methyl chloride was consumed at 350° C. The silane mixture obtained was 40% of the theoretical yield relative to methyl chloride employed, and consisted of methyltrichlorosilane, dimethyldichlorosilane, trimethylchlorosilane and tetrachlorosilane.

EXAMPLE 3

30 g of $SiO_2$ (96.5% by weight of $SiO_2$), having a BET surface area of 20 m²/g, and 90 g of Fe powder (99.5% by weight of Fe), having a surface area of 0.37 m²/g, and 66.5 g of $AlCl_3$ were pelletized with the addition of a small amount of $CH_2Cl_2$. The pellets were dried for 3 hours in a vacuum cabinet at 120° C., and were put into a tubular reactor. The mixture was then heated while methyl chloride was passed in, and the reaction set in at 260° C. At 350° C. all the methyl chloride was consumed. The silane mixture obtained was 40% of the theoretical yield relative to methyl chloride employed, and was composed of 80 mole % of trimethylchlorosilane, 10 mole % of dimethylchlorosilane and 10 mole % of methyltrichlorosilane.

EXAMPLE 4

150 g of $SiO_2$ dust (96.5% by weight of $SiO_2$), having a BET surface area of 20 m²/g, and 150 g of Fe powder (99.5% by weight of Fe, 0.37 m²/g) were pelletized and put into a tubular reactor in layers with a mixture of 40 g of Cu powder and 30 g of $AlCl_3$. The mixture was then heated while methyl chloride was passed in, and the reaction set in at 200° C. At 300° C. all the methyl chloride was consumed. The silane mixture obtained was 50% of the theoretical yield relative to methyl chloride employed, and was composed of 75 mole % of methyltrichlorosilane, 3 mole % of dimethyldichlorosilane, 2 mole % of trimethylchlorosilane and 20 mole % of tetrachlorosilane.

EXAMPLE 5

120 g of SiO$_2$ dust (96.5% by weight of SiO$_2$), having a BET surface area of 20 m$^2$/g, and 240 g of Fe powder (99.5% by weight of Fe, 0.37 m$^2$/g), 266 g of AlCl$_3$ and 6.5 g of Zn powder were pelletized with the addition of a small amount of CH$_2$Cl$_2$. The pellets were dried for 3 hours in a vacuum cabinet at 120° C. and were put into a tubular reactor. The mixture was then heated while methyl chloride was passed through. The reaction set in at 400° C. At 450° C. all the methyl chloride was consumed. The silane mixture obtained was 45% of the theoretical yield relative to methyl chloride employed, and was composed of 55 mole % of trichloromethylsilane, 25 mole % of dichlorodimethylsilane, 12 mole % of tetrachlorosilane and 8 mole % of trimethylchlorosilane.

EXAMPLE 6

90 g of SiO$_2$, 180 g of Fe powder (surface areas and percentages by weight as in Example 5), 199 g of AlCl$_3$ and 9.75 g of CoCl$_2$ were pelletized, dried and put into a tubular reactor as in Example 5. The mixture was then heated while methyl chloride was passed in, and the reactions set in at 270° C. At 300° C. all the methyl chloride was consumed. The silane mixture obtained was 50% of the theoretical yield relative to methyl chloride employed, and was composed of 70 mole % of trimethylchlorosilane, 15 mole % of dimethyldichlorosilane, 10 mole % of methyltrichlorosilane and 5 mole % of tetrachlorosilane.

EXAMPLE 7

60 g of SiO$_2$ dust, 120 g of Fe powder (surface areas and percentages by weight as in Example 5) and 133 g of AlCl$_3$ were pelletized, dried and put into a tubular reactor as in Example 5. The mixture was then heated while ethyl chloride was passed in. The reaction set in at 300° C., and at 350° C. the ethyl chloride employed was sustantially consumed. It was possible to collect, in a cold trap connected in series, a liquid consisting of a silane mixture as well as unreacted ethyl chloride. The silane mixture contained 70 mole % of triethylchlorosilane, 15 mole % of diethyldichlorosilane, 10 mole % of ethyltrichlorosilane and 5 mole % of tetrachlorosilane.

EXAMPLE 8

180 g of SiO$_2$ dust were pelletized and dried as in Example 1 together with 504 g of Fe powder and 72 g of carbon black (surface areas and percentages by weight as in Example 1) and 9.75 g of zinc powder. 190 g of this mixture were put into a tubular reactor and were heated at 1200° C. for 30 hours while argon was passed in. The mixture was then allowed to cool under argon to room temperature. Methyl chloride was then passed in at 50 ml/min, instead of the argon, and the mixture was heated again. The reaction set in at 350° C., and at 380° C. almost all the methyl chloride was consumed. The silane mixture obtained was 45% of the theoretical yield relative to the methyl chloride employed, and was composed of 85 mole % of methyltrichlorosilane and 15 mole % of tetrachlorosilane.

EXAMPLE 9

180 g of SiO$_2$ dust were pelletized and dried as in Example 1, together with 504 g of Fe powder and 72 g of carbon black (surface areas and percentages by weight as in Example 1) and 19.5 g of NiCl$_2$. 190 g of this mixture were put into a tubular reactor and heated at 1200° C. for 30 hours while argon was passed in. The mixture was then allowed to cool under argon to 100° C. Methyl chloride was then passed in at 50 ml/min, instead of the argon, and the mixture was heated again. The reaction set in at 250° C. At 350° C. nearly all the methyl chloride was consumed. The silane mixture obtained was 40% of the theoretical yield relative to the methyl chloride employed, and was composed of 95 mole % of methyltrichlorosilane and 5 mole % of tetrachlorosilane.

EXAMPLE 10

180 g of SiO$_2$ dust were pelletized and dried as in Example 1, together with 504 g of Fe powder and 72 g of carbon black (surface areas and percentages by weight as in Example 1) and 9.5 g of Cu powder. 190 g of this mixture were put into a tubular reactor and heated at 1200° C. for 34 hours while argon was passed in. The mixture was then allowed to cool under argon to room temperature. Ethyl chloride was then passed in at 40 ml/min, instead of the argon, and the mixture was heated again. The reaction set in at 300° C. At 350° C. the bulk of the ethyl chloride employed was converted. The silane mixture obtained was 30% of the theoretical yield relative to the ethyl chloride employed, and was composed of 80 mole % of ethyltrichlorosilane, 10 mole % of diethyldichlorosilane and 10 mole % of tetrachlorosilane.

EXAMPLE 11

420 g of bentonite (58.3% by weight of SiO$_2$), having a BET surface area of 36 m$^2$/g, were mixed with 420 g of Fe powder (99.5% by weight of Fe, 0.37 m$^2$/g), 168 g of carbon black (26 m$^2$/g) and 20 g of Cu powder, and the mixture was pelletized and dried as in Example 1. 200 g of this mixture were put into a tubular reactor and heated at 1100° C. for 12 hours while argon was passed in. The mixture was then allowed to cool under argon to 200° C. Methyl chloride was then passed in at 50 ml/min instead of the argon, and the mixture was heated again. The reaction set in at 330° C. At 350° C. all the methyl chloride was consumed. The silane mixture obtained was 45% of the theoretical yield relative to the methyl chloride employed, and was composed of 70 mole % of methyltrichlorosilane, 5 mole % of dimethyldichlorosilane and 25 mole % of tetrachlorosilane.

While only several embodiments and examples of the present invention have been described, it will be obvious to those skilled in the art that many modifications may be made to the invention without departing from the spirit and scope of the invention.

What is claimed is:

1. A process for the preparation of an organohalosilane of the formula:

$$X_{4-n}SiR_n$$

wherein

R represents a functional group selected from the group consisting of methyl, ethyl, n-propyl, isopropyl, n-butyl, isobutyl, phenyl and tolyl;

X represents a halogen selected from the group consisting of chlorine and bromine; and n is an integer from 1 to 3, inclusive, comprising the steps of:

subjecting to a heat treatment an SiO$_2$-containing material, iron powder, carbon and a catalyst, said heat treatment being at a temperature of 800° to 1400° C.; and thereafter reacting the SiO$_2$-containing material with a hydrocarbon halide of the formula RX wherein R and X are defined as above in the presence of the iron powder, the carbon and the catalyst.

2. The process according to claim 1, wherein said reacting step is carried out at a temperature of 200° to 500° C.

3. The process according to claim 1, wherein the SiO$_2$-containing material has an SiO$_2$ content of 40% to 100% by weight.

4. The process according to claim 1, wherein the SiO$_2$-containing material has a specific surface area, as measured by the BET method of, at least, 0.1 m$^2$/g.

5. The process according to claim 1, wherein the iron powder has an iron content of 70% to 100% by weight.

6. The process according to claim 1, wherein the iron powder has a specific surface area, as measured by the BET method of, at least, 0.1 m$^2$/g.

7. The process according to claim 1, wherein the catalyst is a member selected from the group consisting of an element of the first subgroup of elements in the Periodic Table, an element of the second subgroup of elements in the Periodic Table, and element of the eighth subgroup of elements in the Periodic Table, a halide of an element in the first subgroup of elements in the Periodic Table, a halide of an element in the second subgroup of elements in the Periodic Table, a halide of an element in the eighth subgroup of elements in the Periodic Table, an oxide of an element in the first subgroup of elements in the Periodic Table, an oxide of an element in the second subgroup of elements in the Periodic Table, an oxide of an element in the eighth subgroup of elements in the Periodic Table and a combination thereof.

8. The process according to claim 7, wherein the catalyst is a member selected from the group consisting of Cu$_2$O, CuO, ZnO, CoO, Co$_3$O$_4$, NiO, CuCl, CuCl$_2$, CuBr, CuBr$_2$, ZnC$_2$, ZnBr$_2$, CoCl$_2$, CoBr$_2$, NiCl$_2$, NiBr$_2$ and a combination thereof.

9. The process according to claim 1, wherein the carbon is employed in a finely divided form with a specific surface area, as measured by the BET method of, at least, 0.5 m$^2$/g.

10. A process for the preparation of an organohalosilane of the formula:

$$X_{4-n}SiR_n$$

wherein,

R represents a functional group selected from the group consisting of methyl, ethyl, n-propyl, isopropyl, n-butyl, isobutyl, phenyl and tolyl;

X represents a halogen selected from the group consisting of chlorine and bromine; and n is an integer from 1 to 3, inclusive, comprising the step of:

reacting an SiO$_2$-containing material with a hydrocarbon halide of the formula:

RX wherein R and X are as defined above, in the presence of a member selected from the group consisting of an iron powder, and a trihalide selected from the group consisting of an aluminum trihalide, a boron trihalide and a combination thereof, wherein a halogen of said trihalide is a member selected from the group consisting of chlorine and bromine.

11. The process according to claim 10, wherein said reacting step is carried out at a temperature of 200° to 500° C.

12. The process according to claim 10, wherein the SiO$_2$-containing material has an SiO$_2$ content of 40% to 100% by weight.

13. The process according to claim 10, wherein the SiO$_2$-containing material has a specific surface area as measured by the BET method of, at least, 0.1 m$^2$/g.

14. The process according to claim 10, wherein the iron powder has an iron content of 70% to 100% by weight.

15. The process according to claim 10, wherein the iron powder has a specific surface area, as measured by the BET method of, at least, 0.1 m$^2$/g.

16. The process according to claim 10, further comprising a catalyst selected from the group consisting of an element of the first subgroup of elements in the Periodic Table, an element of the second subgroup of elements in the Periodic Table, an element of the eighth subgroup of elements in the Periodic Table, a halide of an element in the first subgroup of elements in the Periodic Table, a halide of an element in the second subgroup of elements in the Periodic Table, a halide of an element in the eighth subgroup of elements in the Periodic Table, an oxide of an element in the first subgroup of elements in the Periodic Table, an oxide of an element in the second subgroup of elements in the Periodic Table, an oxide of an element in the eighth subgroup of elements in the Periodic Table and a combination thereof.

17. The process according to claim 16, wherein the catalyst is a member selected from the group consisting of Cu$_2$O, CuO, ZnO, CoO, Co$_3$O$_4$, NiO, CuCl, CuCl$_2$, CuBr, CuBr$_2$, ZnCl$_2$, ZnBr$_2$, CoCl$_2$, CoBr$_2$, NiCl$_2$, NiBr$_2$ and a combination thereof.

18. The process according to claim 10, wherein said trihalide is aluminum trichloride for the preparation of an organochlorosilane.

19. The process according to claim 10, wherein said trihalide is aluminum tribromide for the preparation of an organobromosilane.

* * * * *